United States Patent [19]
Leonard et al.

[11] Patent Number: 5,356,795
[45] Date of Patent: Oct. 18, 1994

[54] CLONING CDNAS FOR THE HUMAN INTERLEUKIN-2 RECEPTOR (55 RD PROTEIN)

[75] Inventors: Warren J. Leonard, Washington, D.C.; Warner C. Greene, Potomac, Md.

[73] Assignee: The United States of America as represented by the Secretary of the Department of Health and Human Services, Washington, D.C.

[21] Appl. No.: 837,563

[22] Filed: Feb. 18, 1992

Related U.S. Application Data

[63] Continuation of Ser. No. 373,676, Jun. 28, 1989, abandoned, which is a continuation of Ser. No. 634,380, Jul. 25, 1984, abandoned.

[51] Int. Cl.$^5$ ............................................. C12N 15/12
[52] U.S. Cl. .................................... 435/69.1; 435/69.5; 435/69.52; 435/172.3; 435/240.1; 435/252.3; 435/320.1; 536/23.1; 536/23.5; 530/350
[58] Field of Search .................... 435/69.1, 69.5, 69.52, 435/172.3, 240.1, 252.3, 320.1; 536/235, 23.1

[56] References Cited

U.S. PATENT DOCUMENTS

| | | | |
|---|---|---|---|
| 4,528,335 | 3/1986 | Urland et al. | 458/68 |
| 4,578,335 | 3/1986 | Urdal et al. | 435/68 |
| 4,816,565 | 3/1989 | Honjo et al. | 530/351 |
| 4,845,198 | 7/1989 | Urdal et al. | 530/387 |

FOREIGN PATENT DOCUMENTS 213463  3/1987  European Pat. Off. .

OTHER PUBLICATIONS

Leonard et al., *Immunol.*, 80:6957–6961 (1983).
Sabe et al., *Mol. Biol. Med.*, 2:379–396 (1984).
Leonard et al., *Nature*, 311:626–631 (1984).
Leonard et al., *Science*, 230:633–639 (1985).
Leonard et al., *Nature*, 311:626–631 (1984).
Leonard et al., *Science*, 230:633–639 (1985).
Hatakeyama, et al., *Nature*, 318:467–470 (1985).
Ishida, et al., *Nuc. Acids Res.*, 13:7579–7589 (1985).
Kondo, et al, *Inter.-2 Receptor*, 320:75–77 (1986).
Greene, et al., *Methods in Enzymology*, 150:682–700 (1987).
Greene et al., *Ann. NY Acad. Sci.*, 546:116–121 (1988).
Hatakeyama et al., *Science*, 244:551–556 (1989).
Taniguchi et al. (1983) *Nature* vol. 302 pp. 305–310.
Ullrich et al. (1984) *Nature* vol. 309 pp. 418–425.
Hisataka et al. (1984) *Mol. Biol. Med.* vol. 2, pp. 379–396.
Leonard, W. et al. Oct. 1984, *Nature* 311:626.
Nikaido, T. et al. Oct. 1984, *Nature* 311:631.
Cosman, D. et al. Dec. 1984, *Nature* 312:768.
Greene, W. et al. Jul. 1985, *J. Exp. Med.* 162:363.
Leonard, W. et al. Nov. 1983, *PNAS* 80:6957.

*Primary Examiner*—Garnett D. Draper
*Attorney, Agent, or Firm*—Townsend and Townsend Khourie and Crew

[57] ABSTRACT

The cDNA encoding the human interleukin-2 receptor has been produced, sequenced, and developed for diagnosis of certain T-cell leukemias, in particular the virus associated with adult T-cell leukemia.

14 Claims, 9 Drawing Sheets

```
                                                                                    (100)
      10        20        30        40        50        60        70        80        90       100
      •         •         •         •         •         •         •         •         •         •
GAATTCCCCCCCCCCCGAGAGACTGGATGGACCAAGGGTGACAGCCCAGGGGACCGATCTTCCCATCTCCTCCGGCGGATGCCAA (201)
     110       120       130       140       150       160       170       180       190       200
      •         •         •         •         •         •         •         •         •         •
AAAGAGGCTGACGGCAACTGGGCCTTCTGCAGAGAAAGACCTCCGCTTCACTGCCCGGCTGGTCCCAAGGGTCAGGAAGATGGATTCATACCTGCTGATG
                                                                                   MetAspSerTyrLeuLeuMet (300)
     210       220       230       240       250       260       270       280       290       300
      •         •         •         •         •         •         •         •         •         •
TGGGACTGCTCACGTTCATCATGGTGCCTGGCTGCCAGGCAGAGCTCTGACGATGACCCGAGATCCCACACGCCACATTCAAAGCCATGGCC.
TrpGlyLeuLeuThrPheIleMetValProGlyCysGlnAlaGluLeuCysAspAspProGluIleProHisAlaThrPheLysAlaMetAla (399)
     310       320       330       340       350       360       370       380       390       400
      •         •         •         •         •         •         •         •         •         •
TACAAGGAGGAACCATGTGAATGTGTTGAACTGTAAGAATGCAAGAGAAGAGAGGTTTCCGCAGAATAAAAAGCGGGTCACTCTATATGCTCACTCTGTACAGGAAACTCTAGCCAC
TyrLysGluGluGlnCysGluCysLysArgGlyPheArgArgIleLysSerGlyPheArgGlyIleLysSerGlyPheArgIleLysSerGlyPheArgArgIleLysSerGlyPheArgArgIleLysSerGlyPheArgArgIleLysSerGlyPheArgArgIleLysSerGlyPheArgArgIleLysSerGly 410       420       430       440       450       460       470       480       490       500      (501)
      •         •         •         •         •         •         •         •         •         •
TCGTCCTGGGACAACCAATGTCAATGCACAAGCTCTGCCACTCGGAACCTGAAGACAGAACCTCAAGTGACACCTCAAGAAGAAAGGAAACAGAAAGGAAAAGGAAAAACCACA
SerSerTrpAspAsnGlnCysGlnCysThrSerSerAlaThrArgAsnThrLysGlnValThrProGlnProGluGluGlnLysGluArgLysThrThr
```

```
     1010       1020       1030       1040       1050       1060       1070       1080       1090       1100
       •          •          •          •          •          •          •          •          •          •
AAACCAAAAGAACAAGAATTTCTTGGTAAGAAGCCGGGAACAACAGAAGAGAACAGAAGTCATGAAGCCCAAGTGAAATCAAAGGTGCTAAATGGTCGCCCAGGAG   (1100)

1110       1120       1130       1140       1150       1160       1170       1180       1190       1200
       •          •          •          •          •          •          •          •          •          •
ACATCCGTTGTGCTTGCCTGCGTTTGGAAGCTCTGAAGTCACATCACAGGACACGGGGCAGTGGCAACCTTGTCTCTATGCCAGTCAGTCCATCAGA            (1200)

1210       1220       1230       1240       1250       1260       1270       1280       1290       1300
       •          •          •          •          •          •          •          •          •          •
GAGGGAGGCTACCCACTTCTAAATAGCAATTTCGCGTTGAAGAGGAAGGCAAAACCACTAGAACTCTCCATCTTATTTCATGTATATGTTCATT              (1300)

1310       1320       1330       1340       1350       1360       1370       1380       1390       1400
       •          •          •          •          •          •          •          •          •          •
AAACCATGAATGGTATGGAACTCTCTCCACCTATATGTAGTATAAAGAAAAGTAGGTTTACATTCATTCATTCCAACTTCCAGTTCAGGAGTCCAA            (1400)

1410       1420       1430       1440       1450       1460       1470       1480       1490       1500
       •          •          •          •          •          •          •          •          •          •
GGAAAGCCCCAGCACTAAGCTAAATACAACACACACACTCTACCCTATACAACTGGACATTGTCTGCGGTTCCTTTCTCAGCCGGCTTCTGACTGCT           (1500)

1510       1520       1530       1540       1550       1560       1570       1580       1590       1600
       •          •          •          •          •          •          •          •          •          •
GATTCTCCGTTCACGTTGCCTAATAAACATCCTTCAAGAACTCTGGGCTGCTACCCAGAAATCATTTACCTTGGCTCAATCCTCTAAGCTAACCCCC          (1600)
```

FIG. 4C.

```
     1610      1620      1630      1640      1650      1660      1670      1680      1690      1700
       •         •         •         •         •         •         •         •         •         •
TTCTACTGAGCCTTCAGTCTTGAATTTCTAAAAAACAGAGGCCATGGCAGAATAATCTTTGGTAACTTCAAAACGGGGCAGCCAAACCCATGAGGCAAT (1700)
TTCTACTGAGCCTTCAGTCTTGAATTTCTAAAAAACAGAGGCCATGGCAGAATAATCTTTGGTAACTTCAAAACGGGGCAGCCAAACCCATGAGGCAAT 1710      1720      1730      1740      1750      1760      1770      1780      1790      1800
       •         •         •         •         •         •         •         •         •         •
TCAGGAACAGAGAAGGATGAATCAGGTCCCAGGCAGAGAATCATACTTAGCAAAGTTTTACCTGTGCGTTACTAATTGGCCTCTCTTTAAGAGTTAGTTTCTT (1800)
TCAGGAACAGAGAAGGATGAATCAGGTCCCAGGCAGAGAATCATACTTAGCAAAGTTTTACCTGTGCGTTACTAATTGGCCTCTCTTTAAGAGTTAGTTTCTT 1810      1820      1830      1840      1850      1860      1870      1880      1890      1900
       •         •         •         •         •         •         •         •         •         •
TGGGATTGCTATGAATGATACCCTGAATTGGCCTGCACTAATTGATGTTTACAGGTGGACACAAGGTGCAAATCAATGCTACGTTTCCTGAGAAG (1900)
GAATTC 1910      1920      1930      1940      1950      1960      1970      1980      1990      2000
       •         •         •         •         •         •         •         •         •         •
TGTCTAAAAACACCAAAAGGGATCCGTACATTCAATGTTTATCGAAGGAGGAAAGAAGAAGGAGTGAAGAGGAGAAGGAGGATGGAGGTCACACTGG (2000)

2010      2020      2030      2040      2050      2060      2070      2080      2090      2100
       •         •         •         •         •         •         •         •         •         •
TAGGACGTAACCACGGAAAAGAGCGCATCAGGCCTGGCACGCTGGCTCAGGCCTAACCCCAGCTCCCTAGGAGACCAAGGCGGGAGCATCTCTTGAGG (2100)

2110      2120      2130      2140      2150      2160      2170      2180      2190      2200
       •         •         •         •         •         •         •         •         •         •
CCAGGAGTTTGAGACCAGCTGGGCAGCCTGGCAGCATAGCAAGACACATCCCTACAAAAAATTAGAAATTGGCTGATGTGGTGCATACGCCTGTAGTCCTAGCCA (2200)

2210      2220      2230      2240      2250      2260      2270      2280      2290      2300
       •         •         •         •         •         •         •         •         •         •
CTCAGGAGGCTGAGGCAGGAGGATTGCTTGAGCCCAGGAGTTCGAGGCTGCAGTCAGTCATGATGGCACCACTGCACTCCAGCCTGGGCAACAGAGCAAG (2300)

2310      2320      2330      2340
       •         •         •         •
ATCCTGTCTTTAAGGAAAAAAGACAAGGAATTC
```

CLONING CDNAS FOR THE HUMAN INTERLEUKIN-2 RECEPTOR (55 RD PROTEIN)

This is a continuation of application Ser. No. Ser. No. 07/373,676 filed Jun. 28, 1989, now abandoned, which is a continuation of application Ser. No. 634,380, filed Jul. 25, 1984, now abandoned.

The cDNA encoding the human interleukin-2 receptor has been produced, sequenced, and developed for diagnosis of certain T-cell leukemias, in particular the virus associated with adult T-cell leukemia.

UTILITY STATEMENT

The present invention is useful for diagnosing patients with adult T-cell leukemia. Expression of the gene product, that is, the interleukin-2 receptor protein, is largely limited to the adult T-cell leukemia and activated normal T-cells. The plasmids of this invention, therefore, diagnose and differentiate adult T-cell leukemia from other T-cell leukemias and other malignancies.

In addition, interleukin-2 and its receptor play a vital role in immunodeficiency diseases; the plasmids of this invention are useful as diagnostic tools in determining the adequacy or inadequacy of gene expression for the interleukin-2 receptor in immunodeficiency diseases.

GENERAL DESCRIPTION

The adult T-cell leukemia, a malignancy of mature T-lymphocytes, is uniformly characterized by the expression of surface receptors for T-cell growth factor (interleukin-2). Normal cells do not produce these surface receptors unless activated by mitogenic lectins or antigens.

The present invention represents the first identification of the specific amino acid sequences coding for the human interleukin-2 (IL-2) receptor, as well as a process for expression of a cDNA encoding the human IL-2 receptor.

DESCRIPTION OF THE FIGURES

FIGS. 4A–D illustrate the DNA and protein sequences for the IL-2 receptor. The DNA sequences of clones 3 (top row) and 4 (second row) are shown with amino acid interpretations for the coding regions (third row). The N-terminal amino acid (glutamic acid) and the AATAAA polyadenylation signal that can be used in the 1550 base mRNA are underlined. The T at 895 (under the asterisk) in one of four sequencing runs was a C.

Interleukin-2 (IL-2 or T-cell growth factor) is a lymphokine synthesized and secreted by some T cells after activation with antigen or mitogen in the presence of monocyte derived interleukin-1. IL-2 has permitted long-term growth in vitro of T-cell populations serving helper, suppressor, and cytotoxic functions and has been shown to augment natural killer cell activity. Recent studies have linked IL-2 with acquired immunodeficiency syndrome and select neoplasms.

In order to exert its biologic effects, IL-2 must interact with high affinity specific membrane receptors. This interaction of IL-2 with IL-2 receptors is critical to the evolution of a normal immune response. Resting T cells do not express IL-2 receptors, but receptors are rapidly expressed on T cells following activation with antigen or mitogen. Thus, in contrast to most other hormone-receptor systems, this is an example of one system in which both the ligand and receptor must be induced. IL-2 receptors are not present in most T-cell lines but are uniformly expressed in high numbers in human T-cell leukemia/lymphoma virus-I (HTLV-I), infected T cells, and it is possible that these receptors may be involved in the uncontrolled growth of these cells. HTLV-I is a type C retrovirus etiologically associated with adult T cell leukemia.

The IL-2 receptor has been previously identified as an $M_r=55,000$ glycoprotein on normal activated peripheral blood T cells and as an $M_r=50,000$ glycoprotein on HUT-102B2 cells. These receptors are composed of a peptide precursor of $M_r=33,000$ (denoted p33). This precursor is cotranslationally processed to a p35/p37 doublet by N-linked carbohydrate addition and then processed in the Golgi apparatus to the $M_r=55,000$ (normal activated T cells) or $M_r=50,000$ (HUT-102B2 cells). Mature receptors contain N-linked and O-linked carbohydrate, sialic acid, and are both sulfated and phosphorylated.

GENERAL DESCRIPTION

An anti-Tac monoclonal antibody immunoaffinity column is used to purify large quantities of the human IL-2 receptor from HUT-102B2 cells. This purified protein is used to determine the sequence of the first 29 amino acids of the receptor. On the basis of this sequence, an oligonucleotide probe of 17 nucleotides and 64-fold degeneracy was synthesized. The 17mer identified two mRNAs, 1550 and 3500 bases in length, in HUT-102B2 cells. A lambda gt10 cDNA library prepared from HUT-102B2 cell mRNA was screened with the 17mer and 11 cDNA clones for the receptor were identified. Three of the clones were subcloned into pBR322; selective hybridization of mRNA, translation in the wheat germ cell free translation system, and immunoprecipitation with an anti-IL-2 receptor heteroantiserum confirm the association of these clones with the IL-2 receptor. Further, complete sequencing of each of these three cDNA clones revealed a region of 87 bases that correspond to the 29 amino acids determined by protein sequencing.

SPECIFIC DISCLOSURE

Purification of the IL-2 Receptor

Figure 1:
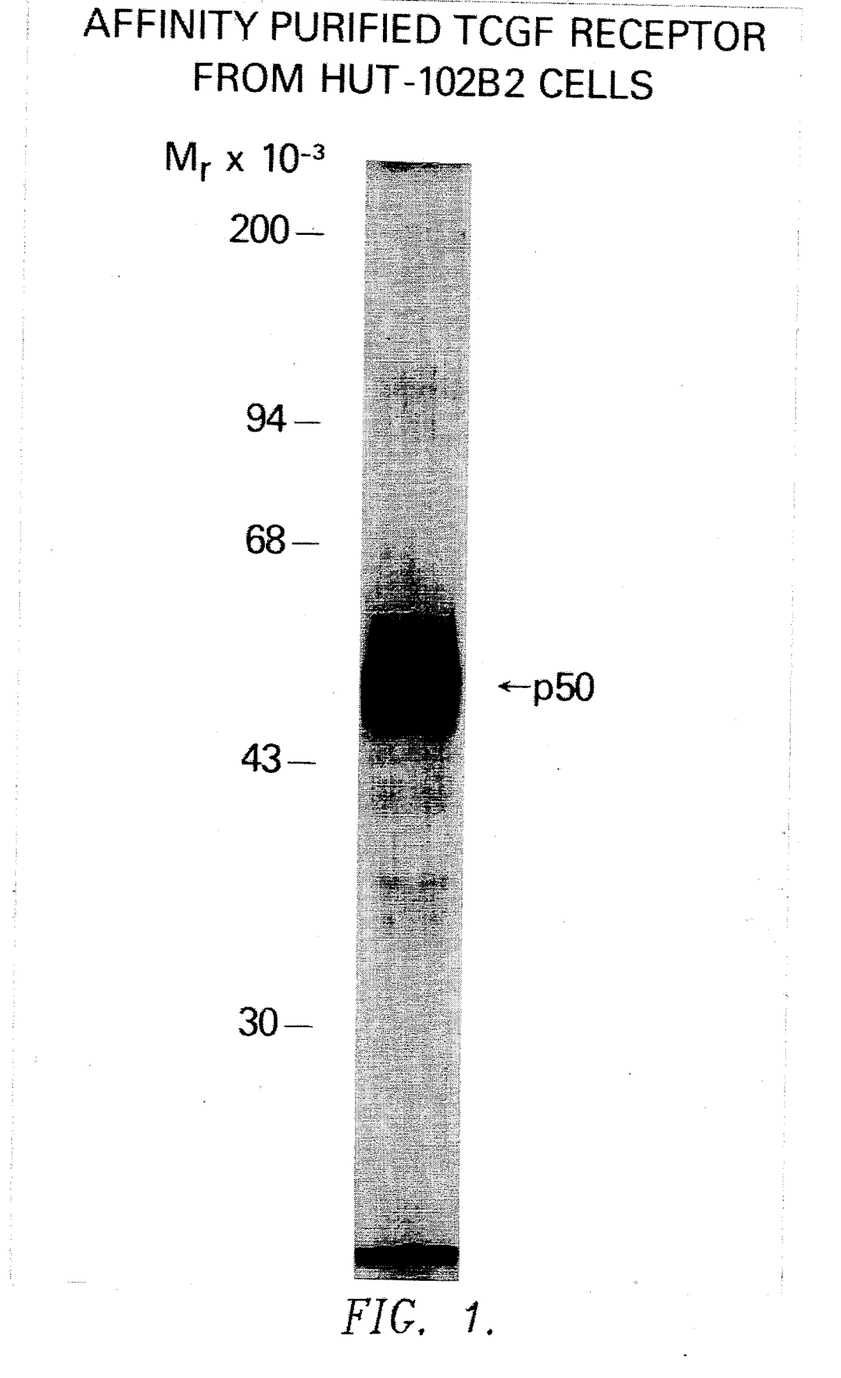
FIG. 1 illustrates the results of purification of the IL-2 receptor protein by the process described in Example 3.

Using anti-Tac, an anti-IL-2 receptor monoclonal antibody, the IL-2 receptor is purified on an immunoaffinity column (FIG. 1). As detailed in the figure legend, NP40 solubilized HUT-102B2 cellular extracts are first passed over a UPC10 control antibody sepharose column and then over the anti-Tac column. Following extensive washing at varying ionic strengths, the IL-2 receptor is eluted with acetic acid, analyzed on SDS gels, and tested for biologic activity. Shown in FIG. 1 is a silver stained gel of material eluted from the affinity column and electrophoresed under reducing conditions. This purified protein blocked over 98% of human IL-2 induced proliferation of a mouse CTLL line, showing that it possesses IL-2 binding activity.

N-terminal Amino Acid Sequencing and Preparation of an Oligonucleotide Probe The N-terminal 29 amino acids of the IL-2 receptor are determined by a combination of sequencing unlabeled purified receptor on a gas phase sequenator and receptor biosynthetically labeled with $^{35}$S-methionine, $^{35}$S-cysteine, $^{3}$H-leucine, $^{3}$H-proline, or $^{3}$H-aspartic acid on a modified Beckman spinning cup sequenator. Results are shown in Table 1, Example 1.

Figure 5:
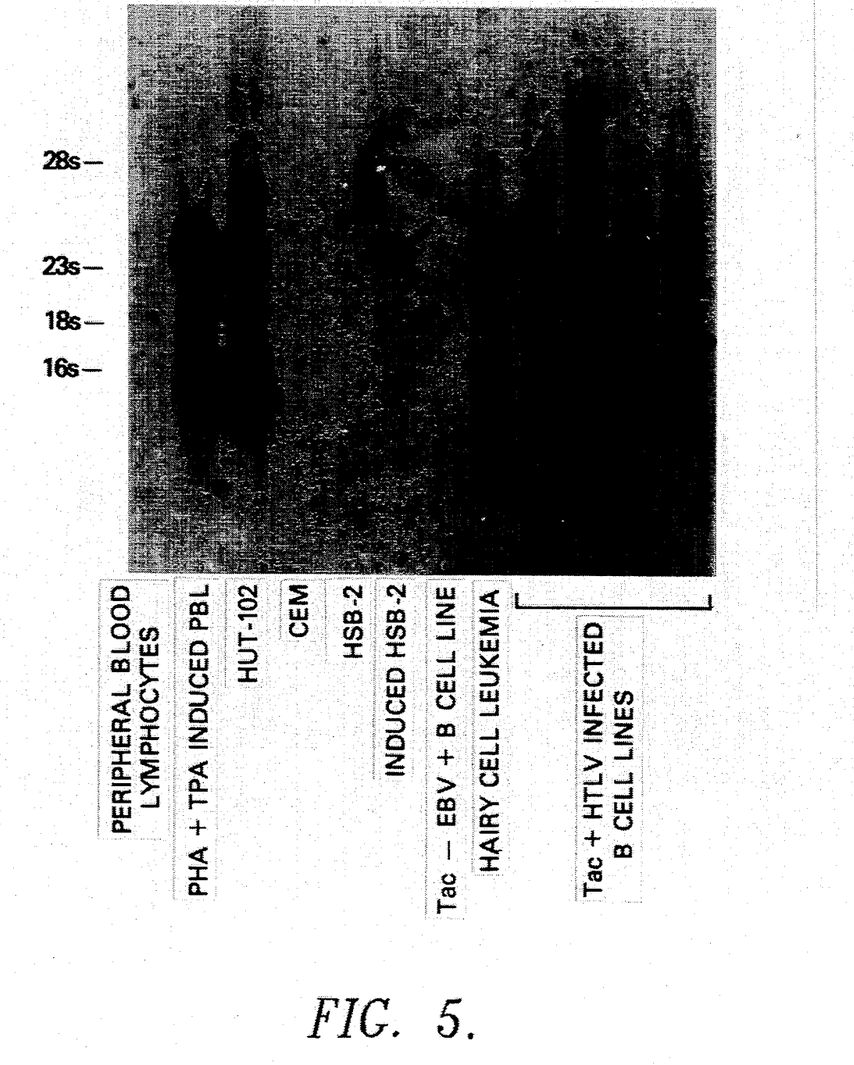
FIG. 5 illustrates the IL-2 receptor mRNA expression in various lymphoid cell types. 10 μg of poly A RNA from each indicated cell type was electrophoresed on a formaldehyde gel, transferred to nitrocellulose and hybridized with nick-translated pIL2R3.

An oligonucleotide probe of 17 nucleotides and 64 fold degeneracy is synthesized homologous to the (−) cDNA strand, corresponding to the sequence cys-asp-asp-asp-pro-pro (amino acids 3–8). The 17mer is end labeled with $^{32}$P-ATP and polynucleotide kinase and hybridized to Northern blots of HUT-102B2 mRNA to confirm that the 17mer identifies at least one mRNA. In fact, two mRNAs, approximately 1550 and 3500 bases long, are identified (identical to those shown in the Northern blot performed with the IL-2 receptor cDNA described below and shown in FIG. 5).

Molecular Cloning of the IL-2 Receptor

A cDNA library is constructed in lambda gt10 from HUT-102B2 cell mRNA as per the protocol of St. John et al (unpublished cDNA cloning method) except that size fractionated double stranded cDNA is purified on glass silica mesh rather than by electroelution. HUT-102B2 cells express 200,000 to 400,000 IL-2 receptors per cell and in these cells, IL-2 receptors account for approximately 0.05% of total cellular de novo protein synthesis. The library consists of four million phage, of which approximately 60% are recombinant. 10 to 20% of these phage contain inserts larger than one kilobase. 500,000 phage from the library are amplified to obtain a high titer library stock.

Figure 6:
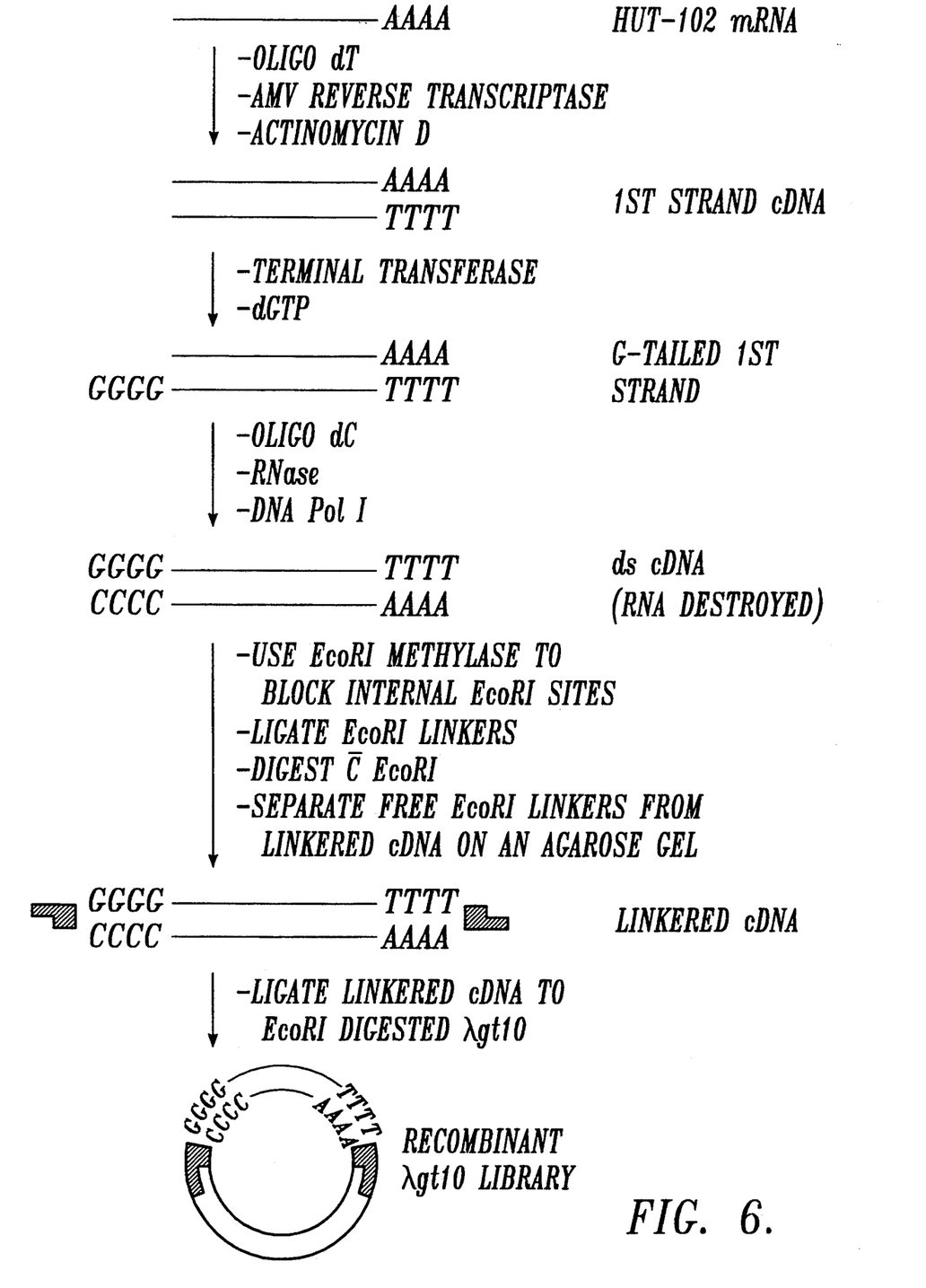
FIG. 6 is a schematic view of the formation of a cDNA library.

The cDNA library is formed by the following process (illustrated in FIG. 6). A cell that expresses the IL-2 receptor, preferably a HUT-102B2 cell mRNA (which contains a poly-A tail), oligo-dT, amv reverse transcriptase and actinomycin D are added to the mRNA to form first strand cDNA. First strand cDNA is G-tailed by adding dGTP and terminal transferase. Second strand synthesis was performed using DNA polymerase 1, oligo dC, and RNAase. Ribonuclease is added at this point to destroy the original RNA template. The resulting double stranded cDNA is then treated with EcoRI methylase to block internal EcoRI sites. EcoRI linkers are then ligated to the cDNAs. The linkered cDNA is then digested with EcoRI and the linkered double stranded cDNA purified from free linkers on an agarose gel. cDNAs larger than 500 bases are cut out of the gel, and the cDNAs recovered on silica glass mesh. The cDNAs are then ligated to EcoRI digested lambda gt10 to form a recombinant cDNA library in lambda gt10. The library generated contained 4,000,000 phage, of which 2,400,000 contained cDNA inserts.

Approximately 200,000 recombinant phage from the amplified library are screened with a $^{32}$P-kinased 17mer. Phage plaques are bound to nitrocellulose, prehybridized overnight at 50° C. in 6X NET (1X NET is 0.15M NaCl, 0.001M EDTA, 0.015M tris, pH 7.5), 5X Denhardts, 0.5% NP40, 200 µg/ml salmon sperm DNA, and then hybridized with the 17mer for 24–48 hours in the same buffer containing 10% dextran sulfate. Filters are washed four times for five minutes in 6X SSC on ice, then for 1 minute at 50° C., and then transferred immediately to 6X SSC on ice, blotted dry, and autoradiographed. On primary screen, 31 candidate clones are identified, of which 12 are positive on secondary and tertiary screens. When the cDNA inserts are excised and probed with the 17 mer, 11 of the 12 are identified as true positives. The cDNAs range in size from approximately 900 to 2300 base pairs.

Figure 2:
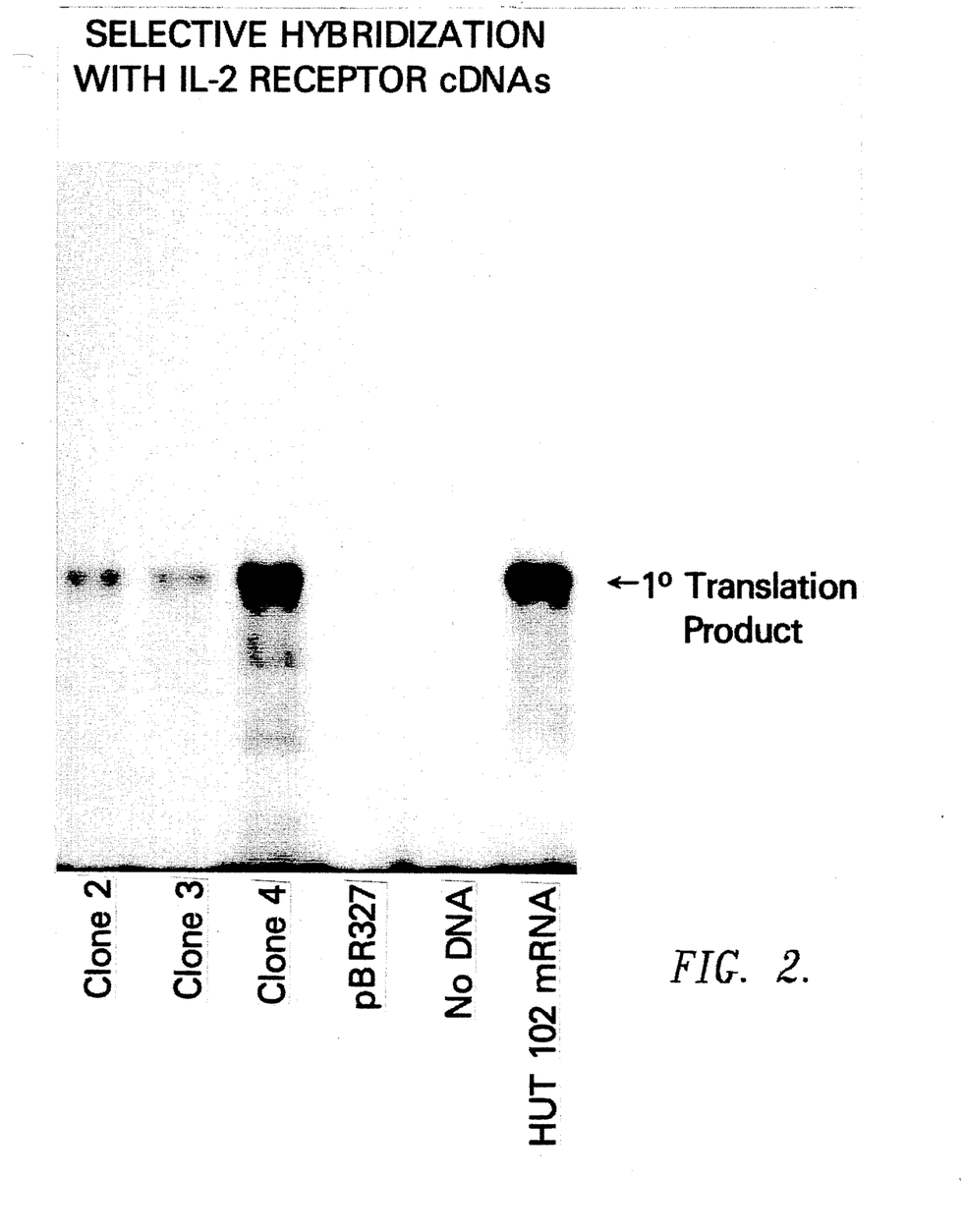
FIG. 2 illustrates the results of identification of the primary translation product of the IL-2 receptor by the process described in Example 4.

Two of these clones (identified as clones 3 and 4, which are approximately 1600 and 2300 bases long, respectively) exhibited preferred characteristics. cDNA inserts from each are subcloned into the EcoR1 site of a suitable plasmid, preferably pBR322 (clones now denoted pIL2R3 and pIL2R4) to facilitate large scale preparation of inserts. Selective hybridization experiments are performed. As shown in FIG. 2, both recombinant plasmids hybridized mRNA that, when translated in a wheat germ cell free translation system and immunoprecipitated with a rabbit heteroantiserum to the IL-2 receptor, yields the same sized primary translation product precipitated directly from translations with HUT-102B2 mRNA (shown on the right). In contrast, control pBR327 and nitrocellulose without DNA added does not selectively hybridize to the IL-2 receptor mRNA. These data confirm that clones 3 and 4 are receptor associated clones.

Nucleotide Sequence of the cDNA Inserts of pIL2R3 and pIL2R4

Figure 3:
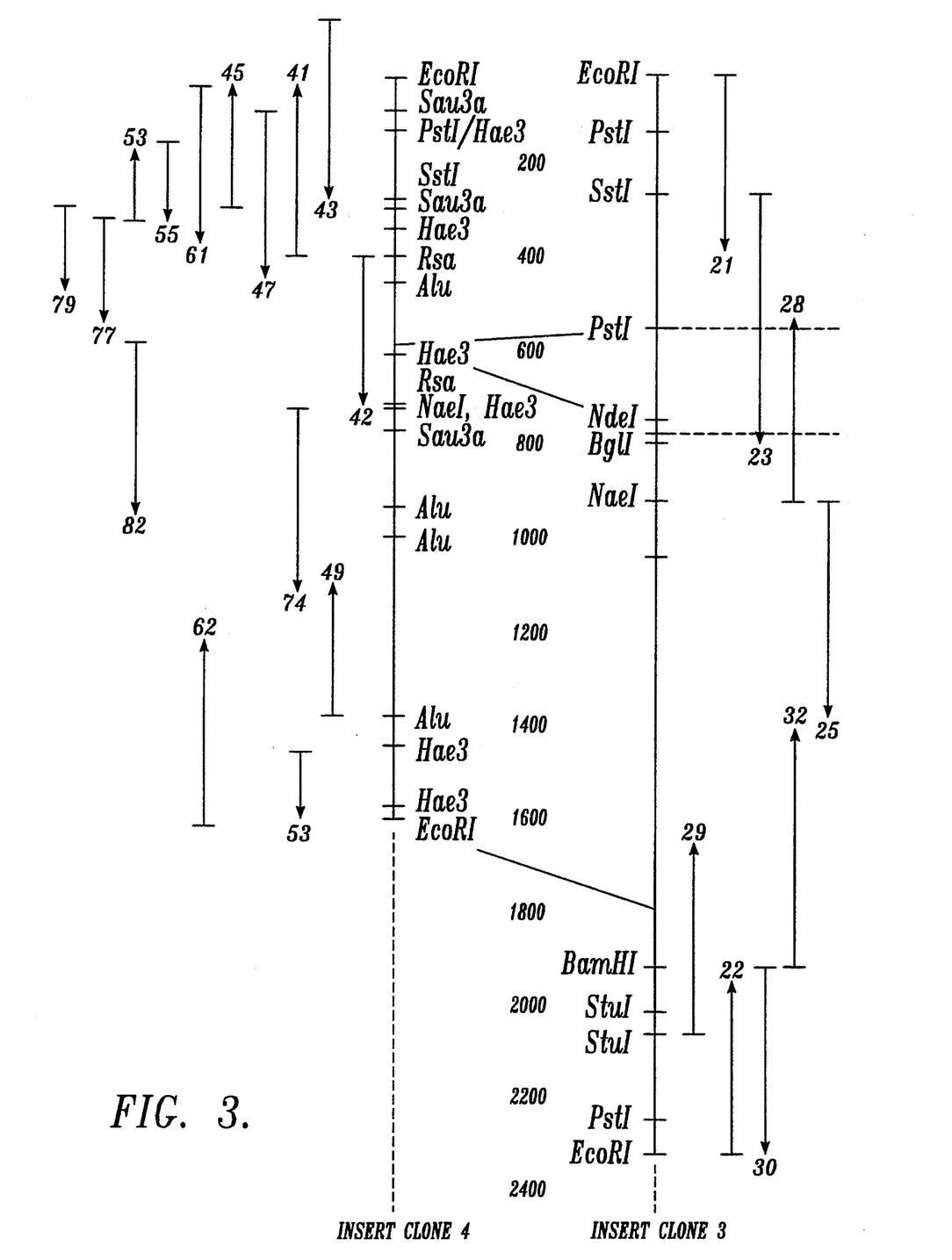
FIG. 3 shows the restriction map of clone 3 and 4. Note the location (marked by the vertical dashed lines) of the splicable region in clone 3 that is not present in clone 4. Clone 3 was directionally cloned into M13 bacteriophage using EcoRI, SstI, NaeI, BamHI, and StuI restriction sites. Clone 4 was cloned and sequenced in M13 bacteriophage using 4 base restriction enzymes RsaI, HaeIII, AluI, and Sau3aI.
Figure 4A:
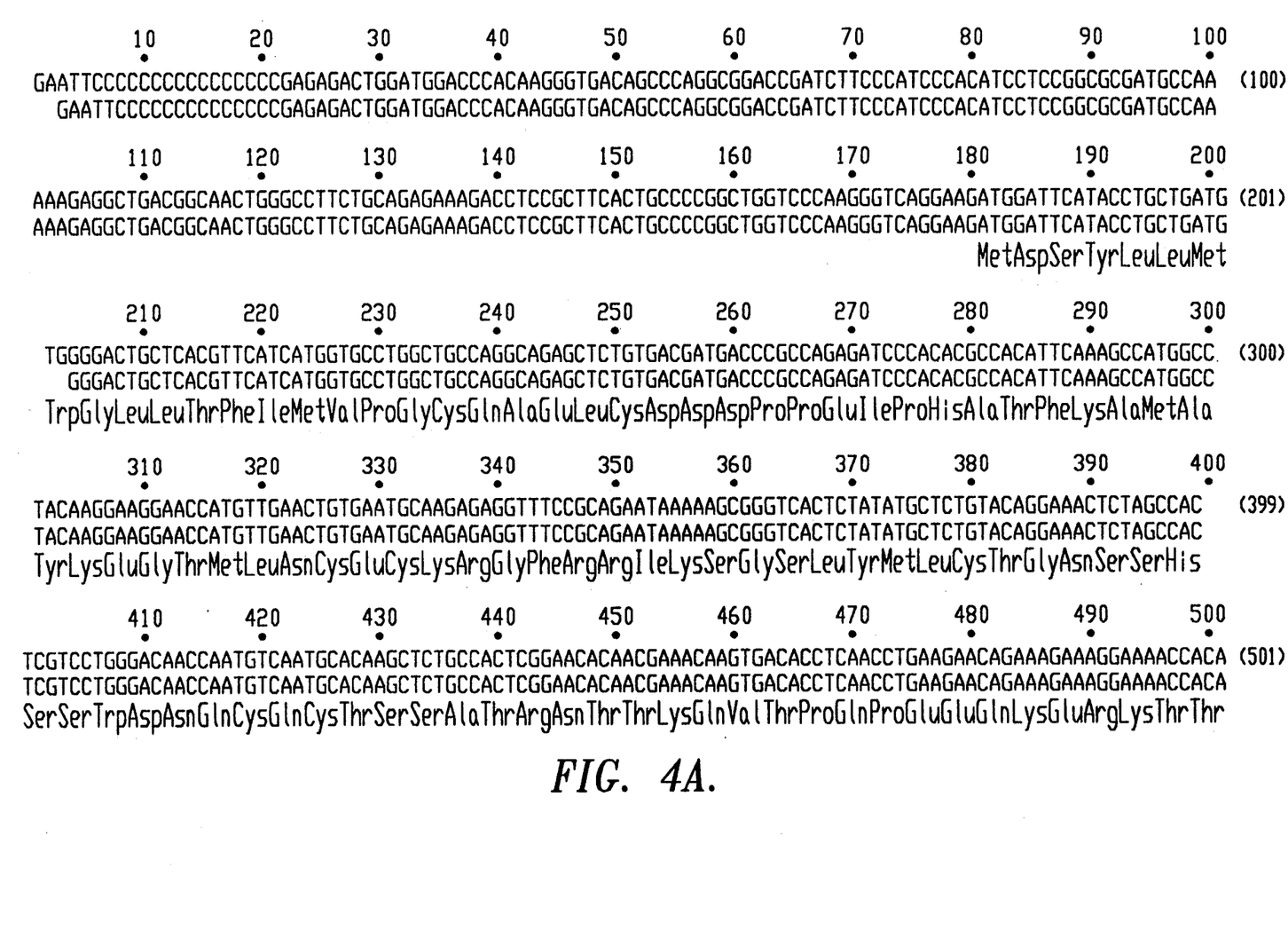
Figure 4C:
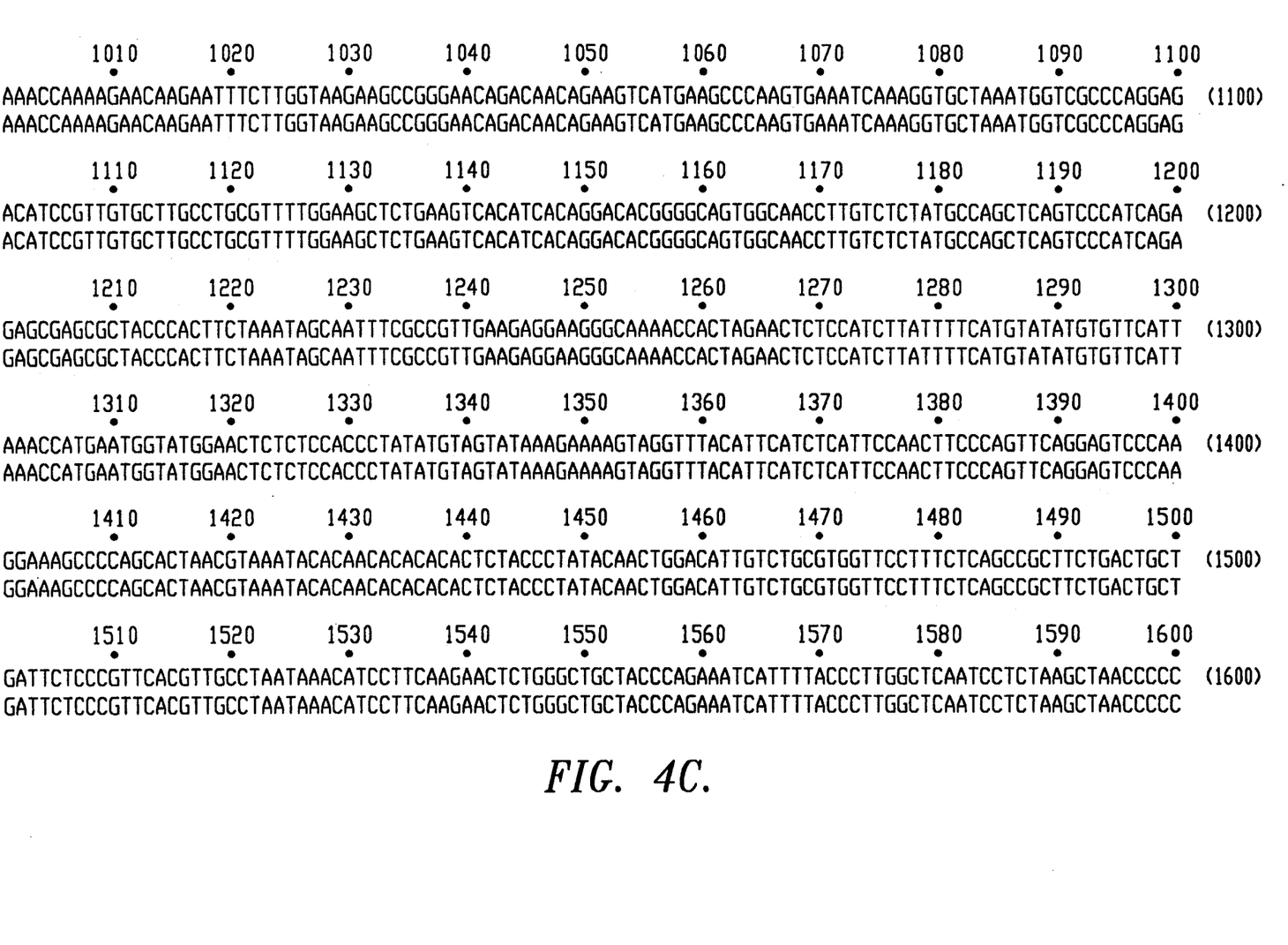

The inserts of pIL2R3 and pIL2R4 are subcloned into M13 bacteriophage and their complete nucleotide sequences are determined by the dideoxy chain termination method. The restriction maps and sequencing strategy of the inserts of pIL2R3 and pIL2R4 are indicated in FIG. 3, and the DNA sequences for each are shown in FIG. 4.

The DNA sequences are analyzed and compared on an IBM system 370 computer. Clones 3 and 4 each contain large open reading frames, including the 87 bases corresponding to the 29 amino acids determined by protein sequencing. Amino acid 1 is located at base 244. There are three potential initiator ATGs in the correct reading frame at amino acid positions −21, −15, and −7 (bases 181–183, 199–201, and 223–225, respectively). Signal peptides are normally 15 to 30 amino acids length. Preliminary data from sequencing of an $^{35}$S-methionine labeled primary translation product indicates that the initiation site is at amino acid −21. All clones had C-tails at the 5′ end added during cDNA synthesis but lack 3′ poly A tails. The poly A tails may have been lost due to the 5′ to 3′ exonuclease activity in second strand synthesis since the holoenzyme DNA polymerase I was used instead of the Klenow fragment.

Analysis of the sequence of clones 3 and 4 revealed that they differ in two principal ways. First, clone 4 encodes a smaller peptide (179 amino acids, 20,070 daltons) than does clone 3 (251 amino acids, 28,437 daltons). These sizes do not include a leader sequence of 21 amino acids. These proteins share the same amino (base 244) and carboxy termini (TAG at 997–999 in clone 3); however, clone 4 lacks 216 bases (72 amino acids) in the middle of the protein coding region. In clone 3, this region is present and is bounded by the sequence TTCCAGGT on both sides (bases 542–549 and 758–765). It therefore represents a typical messenger RNA processing splice site. Second, clone 3 extends further 3' than clone 4; however, neither clone reaches a terminal AATAAA. It is of interest that both clones 3 and 4 contain the same internal AATAAA (bases 1523–1528 in clone 3) 3' to the end of the coding region. These AATAAAs are not utilized in the mRNAs corresponding to these cDNAs, but they represent potential alternate polyadenylation addition signals.

Expression of an IL-2 Receptor cDNA in COS-1 Cells

The molecular weight for the IL-2 receptor is predicted to be 33,000 daltons based on apparent $M_r$ on SDS gels for the putative peptide precursor. Despite the variability that can exist in migration of different proteins on SDS gels due to variable association with SDS up to the theoretical level of 1.4 grams SDS per gram of protein, clone 3, which encoded the larger protein product, appears to be the correct one. To prove this, it was essential to express the cDNAs. The inserts from pIL-2R3 and pIL-2R4 were excised with EcoR1 and ligated into the EcoR1 site of the expression vector pcEXV-1. This places the cDNA under the control of the SV40 early promoter and SV40 enhancer. These constructs, containing the inserts of clones 3 or 4 in the proper orientations, were transfected into COS-1 cells by calcium-phosphate precipitation, and the cells were evaluated 72 hours later for expression of IL-2 receptors. As shown in Table 2, Example 2, cells transfected with control pBR322 did not bind either $^3$H-IL-2 or $^3$H-Anti-Tac. In contrast, cells transfected with the insert from pIL2R3 bound both $^3$H-IL-2 and $^3$H-anti-Tac. This binding was specific as excess unlabeled IL-2 and anti-Tac completely blocked the binding. Transfection with pcEXV-1 containing the clone 4 insert, which encodes a smaller protein than clone 3, did not result in the expression of IL-2 receptors. These data demonstrate that clone 3 encodes a functional IL-2 receptor and that clone 4 does not.

The IL-2 Receptor Encode by a Single Gene

The number of genes corresponding to the IL-2 receptor were evaluated by hybridizing nick translated $^{32}$P-pIL2R3 to genomic DNA digested with EcoRI and BamHI. In the EcoRI digests, two fragments, the larger of which is 5800 bases long, were identified; in the BamHI digests, a single 7500 base fragment was identified. These data indicate a single copy gene but do not exclude a recently duplicated gene.

EXAMPLE 1
TABLE 1

H$_2$N—glu—leu—<u>cys</u>*—<u>asp</u>*—<u>asp</u>*—<u>asp</u>*—<u>pro</u>*—<u>pro</u>*—glu—ile—pro*—his— ala*—thr—phe—lys—ala*—met—ala—tyr—lys—glu—gly—thr—met—leu*— asn*—cys—glu

Purified receptor from the affinity column was subjected to automated Edman degradation on a gas phase sequenator, and samples analyzed by high performance liquid chromatography. Some positions were determined or confirmed by sequencing receptor biosynthetically labeled with $^3$H-aspartic acid, $^3$H-leucine, or $^3$H-proline, or with $^{35}$S-methionine or $^{35}$S-cysteine. For incorporation, cells were grown in the presence of amino acid free RPMI, 5% fetal bovine serum (as a source of unlabeled amino acids), and 1 to 5 mCi of the radiolabeled amino acid. For aspartic acid, labeling was performed in the presence of 1 mM amino oxyacetic acid. All radioactive amino acids used were the highest specific activity available from Amersham and/or New England Nuclear. The positions determined or confirmed by radiolabeled sequencing are noted with asterisks. The positions underlined above represent the amino acids on which the oligonucleotide DNA sequence was based.

EXAMPLE 2

TABLE 2

| Transfected plasmid | Experiment 1 | | Experiment 2 | |
|---|---|---|---|---|
| | Unlabeled L-2 added | $^3$H-IL-2 dpm bound | Unlabeled anti-Tac added | $^3$H-anti-Tac dpm bound |
| pBR322 | − | 25 | − | 60 |
| pBR322 | + | 17 | + | 150 |
| pcEXV-1-IL2R3 | − | 562 ± 11 | − | 28,588 ± 1548 |
| pcEXV-1-IL2R3 | + | 62 ± 18 | + | 261 ± 0 |
| pcEXV-1-IL2R4 | − | 12 ± 10 | − | 252 ± 9 |
| pcEXV-1-IL2R4 | + | 12 ± 3 | + | 171 ± 39 |

0.5 μg of clone 3 or 4 insert were ligated to 0.25 μg of EcoRI digesated and alkaline phosphatase treated pcEXV-1. The plasmid was transformed into competent cells and recombinant plasmids with the inserts in the correct orientations selected. The plasmids were prepped and 5 μg of each recombinant plasmid or of control pBR322 were transfected into COS-1 cells using calcium-phosphate precipitation. The cells were grown overnight, media changed, and then grown for 48 hours. The cells were washed, incubated for 90 min. at 4° C. with RPMI 1640 medium containing 3% fetal bovine serum. In Experiment 1,45,000 dpm of $^3$H-IL-2 with or without a 500-fold excess of unlabeled IL-2 were added. In Experiment 2,194,000 dpm of $^3$H-anti-Tac with or without a 1000 fold excess of anti-Tac were added. The cells were then washed four times in medium containing fetal bovine serum and dissolved in 1 ml 0.1N NaOH. The cell associated radioactivity was then determined. The machine background of 44 dpm has been subtracted from each data point. Data are expressed as mean dpm bound±standard deviation determined from duplicate plates. For reference, HUT-102B2 cells, which have approximately 300,000 total (high plus low affinity) IL-2 receptors per cell, bound either 1,160 of 6,500 dpm of $^3$H-IL-2 or 34,500 of 92,100 dpm of $^3$H-anti-Tac added per $10^6$ HUT-102B2 cells.

EXAMPLE 3

Purification of IL-2 Receptor Protein

Anti-Tac and control UPC10 immunoaffinity columns were prepared by coupling purified anti-Tac and UPC10 monoclonal antibodies to cyanogen bromide activated sepharose. Approximately $8 \times 10^{10}$ HUT-102B2 cells were grown in 10% fetal bovine serum/RPMI medium, harvested by centrifugation, washed twice in phosphate buffered saline, and solubilized in 100 ml of extraction buffer (10 mM tris pH 7.4, 0.15M NaCl, 100 µg/ml phenylmethylsulfonyl fluoride (PMSF), 0.5% NP40) for 45 min on ice with periodic vortexing. An additional 100 ml of extraction buffer was then added, and the cells solubilized for an additional 30 min on ice. Extracts were then centrifuged in a Beckman Ti60 rotor at 37,000 rpm for 30 min at 4° C. The top lipid layer was discarded, and the supernatant collected and stored in aliquots in liquid nitrogen. For each protein prep, 10 ml aliquots of the extracted cells were passed over a UPC10 column 4 times, and then over an anti-Tac column 3 times. The anti-Tac column was washed with 40 ml extraction buffer, 40 ml of 10 mM tris pH 7.5, 0.5M NaCl, 0.5% NP40, 25 ml of 10 mM tris pH 7.5, 0.1% NP40, and then 10 ml of 10 mM tris pH 7.5. The anti-Tac column was eluted with 3 ml of 2.5% (v/v) acetic acid. The eluted protein was lyophilized, resuspended in 100 µl water, and 5 µl analyzed on SDS-polyacrylamide gels under reducing conditions, and the gels silver stained to assess yield and purity. The columns were then washed extensively and stored in extraction buffer.

EXAMPLE 4

Preparation of a rabbit heteroantiserum, identification of the primary translation product for the IL-2 receptor and selective hybridization Purified IL-2 receptor protein (approximately 3 to 5 µg) was divided into equal aliquots, one boiled in 1% SDS for 5 min and one not treated, each emulsified with an equal volume of complete Freund's adjuvant and injected subcutaneously into multiple sites in a New Zealand white female rabbit. The rabbit was boosted (analogous injections in complete Freund's adjuvant) at six weeks. The rabbit was phlebotomized weekly and the ability of the serum to block $^3$H-anti-Tac binding to activated T cells and to precipitate the IL-2 receptor was assessed. The antiserum specifically precipitated the same 50,000 dalton band from HUT-102B2 cells as did anti-Tac and did not appear to specifically identify any other proteins. Total cellular RNA was isolated from HUT-102B2 cells. The poly A fractions were isolated on oligo-dT cellulose and translated for two hours at room temperature in a wheat germ cell free translation system. The translation mix was then boiled in 2% SDS, cooled to room temperature, diluted to five times the original volume with final concentrations of 1×PBS, 1% triton-X-100, and 100 µg/ml PMSF. The mix was cleared with normal rabbit serum and Cowan I strain staphylococcus, immunoprecipitated with the heteroantiserum or preimmune serum as previously described, and electrophoresed on a gel (sixth lane).

Selective hybridization was performed with DNA from pIL2R2, pIL2R3, and pIL2R4, and with pBR327 and omission of DNA as controls. DNA was linearized by digestion with SalI prior to binding to nitrocellulose. HUT-102B2 mRNA was selectively hybridized, translated, and precipitated with the anti-IL-2 receptor heteroantiserum (first five lanes).

EXAMPLE 5

IL-2 Receptor mRNA Expression and Its Association With HTLV-I Infection

By using an IL-2 receptor cDNA, the pattern of expression of IL-2 receptor mRNA was found to parallel the expression of Tac antigen. Resting Tac negative peripheral blood T cells contained few, if any, IL-2R mRNA copies (FIG. 6, lane 1). However, Tac positive peripheral blood T cells activated with PHA plus phorbol myristic acetate (PMA) (lane 2), and HTLV-I infected HUT-102B2 cells (lane 3) contained two mRNAs (1550 and 3500 bases), which hybridized to nick translated IL-2 receptor cDNA. Tac negative CEM and HSB-2 acute lymphocytic leukemic T cell lines did not contain IL-2 receptor mRNA; however, induction of Tac expression on HSB-2 cells with PMA was associated with the appearance of IL-2 receptor mRNA. It is of interest that the induced HSB-2 cells expressed the two mRNAs in significantly different relative quantities. A Tac negative EBV transformed B cell line was negative, but Tac positive Hairy Cell Leukemia cells and Tac positive HTLV infected EBV negative B cell lines expressed both IL-2 receptor mRNAs. These data provide a pattern of mRNA expression consistent with the knowledge of which cells react with anti-Tac and express IL-2 receptors and demonstrate that even in B cells, HTLV-I infection is associated with IL-2 receptor mRNA expression.

EXAMPLE 6

Analysis of the sequence data in both clones 3 and 4 revealed that both cDNAs contained 2 AATAAA sequences corresponding to the potential polyadenylation addition signal present in eukaryotic mRNAs (the first is in the coding region, bases 351–356, and the second is 3' to the coding region, beginning at base 1523 in clone 3, and is underlined in FIG. 4). However, these particular AATAAAs are apparently not utilized in clones 3 and 4 as no polyadenylation tails are noted and the cDNAs continue 3' to the AATAAA sites. The functional AATAAAs in clones 3 and 4 are 3' to the ends of the clones of this invention. The 1550 and 3500 base long mRNAs may differ primarily by the polyadenylation signal used. In this model, the 1550 base mRNA utilizes the AATAAA beginning at base 1523 and underlined in FIG. 4, whereas the longer mRNA uses a more distal signal site. The BamHI-EcoRI and NcoI-RI 3' fragments of clone 3 (bases 1921 to 2335 and 1642 to 2335, respectively) hybridize only to the 3500 base mRNA, confirming that the cDNA sequence 3' to the AATAAA is present in the mRNA. Since this sequence is not repeated in the cDNA 5' to the AATAAA, it is also not a cloning artifact. The smaller 1550 mRNA does not similarly hybridize to the BamHI-EcoRI probe and therefore uses the underlined AATAAA. It is of interest that in the BamHI-EcoRI region, there are two sets of repeated sequences (2080–2113 is 82% homologous to 2213–2247, and 2115–2137 is 87% homologous to 2279–2301). Clone 4 does not apparently arise from either message noted; however, its message is identical to that of clone 3 except that the intron region has been removed. Such an mRNA (approximately 3300 bases) would not be resolved from the 3500 base mRNA corresponding to clone 3 on the Northern blot.

Statement of Deposit

Plasmids pIL2R3 and pIL2R4 have been deposited in the ATCC in their patent program, which assures permanence of the deposit and release thereof upon the granting of a patent, and said deposit has been made prior to the filing of this patent application. pIL2R3 has ATCC No. 39775 and pIL2R4 has ATCC No. 39776.

We claim:

1. An isolated and purified recombinant DNA molecule comprising bp 181–999 in FIG. 4 which encodes a human interleukin-2 receptor.

2. A DNA molecule as in claim 1, wherein the sequence is operably linked to a promoter.

3. The DNA molecule of claim 2 which is pIL-2R3 designated as ATCC No. 39775.

4. A method to produce interleukin-2 receptor polypeptide comprising:
   forming a cDNA library from lambda phage and donor cells which express interleukin-2 receptor protein to form recombinant phage;
   identifying selected recombinant phage comprising a DNA sequence comprising bp 181–999 of FIG. 4 which encodes a human interleukin-2 receptor;
   removing the DNA sequence from the selected recombinant phage and inserting the DNA sequence into a vector;
   transfecting the vector into a host cell capable of expressing interleukin-2 receptor protein and isolating the interleukin receptor protein.

5. The method of claim 4, wherein the donor cells are HUT-102B2 cells.

6. The method of claim 4, wherein the vector is pcEXV-1.

7. The method of claim 4, wherein the selected recombinant phage is identified by hybridizing DNA from the recombinant phage with a nucleotide probe.

8. The method of claim 7, wherein the nucleotide probe comprises bp 244–999 in FIG. 4.

9. The method of claim 7, wherein the nucleotide probe comprises bp 250–267 in FIG. 4.

10. A method to produce interleukin-2 receptor polypeptide, comprising:
    transfecting a vector comprising a DNA sequence comprising bp 181–999 of FIG. 4 which encodes a human interleukin-2 receptor into a host cell capable of expressing interleukin-2 receptor protein; and
    isolating the interleukin-2 receptor polypeptide.

11. A method for producing a human interleukin-2 receptor which comprises:
    growing eukaryotic cells transfected with a DNA construct which comprises a bp 244–999 in FIG. 4 and
    purifying interleukin-2 receptor from the cells.

12. The method of claim 11, wherein the cells are mammalian cells.

13. The method of claim 11, wherein the DNA construct is pcEXV-1-IL2R3.

14. The method of claim 11, wherein the interleukin-2 receptor is purified on an immunoaffinity column.

* * * * *